(12) United States Patent
Gillespie

(10) Patent No.: US 6,982,090 B2
(45) Date of Patent: Jan. 3, 2006

(54) MORE EASILY VISUALIZED PUNCTUM PLUG CONFIGURATIONS

(76) Inventor: Donald E. Gillespie, 4629 Platt Rd., Ann Arbor, MI (US) 48108

( * ) Notice: Subject to any disclaimer, the term of this patent is extended or adjusted under 35 U.S.C. 154(b) by 596 days.

(21) Appl. No.: 09/852,519

(22) Filed: May 10, 2001

(65) Prior Publication Data

US 2002/0169409 A1    Nov. 14, 2002

(51) Int. Cl.
A61B 3/16 (2006.01)
A61B 8/10 (2006.01)
A61F 2/14 (2006.01)

(52) U.S. Cl. .......... 424/427; 600/318; 600/398; 600/402; 424/9.6; 424/9.61; 424/9.62; 424/9.81; 424/10.1; 424/10.3; 424/429; 424/422; 424/428

(58) Field of Classification Search .......... 424/9.6, 424/9.61, 9.81, 9.62, 10.1, 10.3, 427–429, 424/422; 600/318, 398, 402
See application file for complete search history.

(56) References Cited

U.S. PATENT DOCUMENTS

| | | | | |
|---|---|---|---|---|
| 3,949,750 A | * | 4/1976 | Freeman | 128/260 |
| 4,959,048 A | * | 9/1990 | Seder et al. | 604/9 |
| 5,178,635 A | * | 1/1993 | Gwon et al. | 623/4 |
| 5,300,020 A | * | 4/1994 | L'Esperance | 604/9 |

* cited by examiner

Primary Examiner—Sreeni Padmanabhan
Assistant Examiner—Shahnam Sharareh
(74) Attorney, Agent, or Firm—Gifford, Krass, Groh, Sprinkle, Anderson & Citkowski, PC

(57) ABSTRACT

An improved punctum plug is more easily visualized when positioned within a punctual canal of a recipient. The body of the plug features an outwardly exposed surface when properly positioned, and a substance causing at least the outwardly exposed surface to contrast with surrounding tissue, such that the use of the substance causes the plug to be more easily visualized than if the substance were not present. The substance, which may be disposed on the outwardly exposed surface or within the body of the plug, may include a saturated coloration, or may be phosphorescent, fluorescent or otherwise operative to reflect or re-radiate light to assist in visualization. For example, the substance may include an organic or inorganic phosphor or fluorescent material, reflective beads, quantum dots, a dye or pigment. Such reflection or re-radiation may occur at the same or different wavelength(s) compared to the illumination wavelength(s), whether or not either or both are within the visible part of the spectrum. If outside the visible region, a detector may be employed according to the invention for detecting the radiated light. A system for determining whether or not a punctum plug is positioned within the punctal canal of a person's eye is also enclosed, including at least one optical element permitting the eye to view itself, to be viewed by the other eye, or by a second person.

8 Claims, 1 Drawing Sheet

MORE EASILY VISUALIZED PUNCTUM PLUG CONFIGURATIONS

FIELD OF THE INVENTION

This invention relates generally to the punctum plug and in particular, to plugs and apparatus which enable a plug to be more easily visualized following insertion.

BACKGROUND OF THE INVENTION

Tears are provided to the human eye to lubricate them, supply nutrients and guard against environmental contaminants. The tears are secreted by the lachrymal gland, and the excess fluid is carried away by lachrymal or punctal canals into the lachrymal sac, and along the nasal duct into the cavity of the nose.

A condition called "dry eye" may occur when inadequate tears are produced. Generally, this is the result of improper body chemistry, injury, or the aging process. This condition may affect either or both of the eyes and causes the eyes to feel scratchy and irritated. Artificial eye drops may provide temporary relief from the problem, but a long term solution is desirable.

One long-term solution involves the reversible closing of one of the drain ducts of the affect eye. This is done by inserting a plug into one of the ducts, or punctual canals. Typically, this is a clinical procedure requiring less than a half hour. However, a problem often arises after the plug is inserted because the body may eject the plug from the canal, or it may be "rubbed out" by the recipient. In either event, the value of the treatment is lost. Therefore, the recipient has great interest in knowing the plug remains in place.

As the plug is extremely small, generally being less than a millimeter in diameter and a millimeter or so in length, it is very difficult to see. Also, the plug is made all the more difficult to see because it is currently made of Silastic rubber that is naturally flesh colored and translucent and is therefore not easily seen. It is the objects of this invention to make the punctum plug readably visible or detectable to the recipient or caregiver, and thereby help the recipient determine that the plug remains properly in place.

SUMMARY OF THE INVENTION

This invention improves upon the existing art by providing a punctum plug which is more easily visualized when positioned within a punctual canal of a recipient. Broadly, a plug according to the invention includes a body having an outwardly exposed surface when properly positioned, and a substance causing at least the outwardly exposed surface to contrast with surrounding tissue, such that the use of the substance causes the plug to be more easily visualized than if the substance were not present. The rest of the plug body may be composed of any suitable material, including those presently used in the manufacture of such devices.

The substance, which may be disposed on the outwardly exposed surface or within the body of the plug, may include a saturated coloration, or may be phosphorescent, fluorescent or otherwise operative to reflect or re-radiate light to assist in visualization. For example, the substance may include an organic or inorganic phosphor or fluorescent material, reflective beads, quantum dots, a dye or pigment. Such reflection or re-radiation may occur at the same or different wavelength(s) compared to the illumination wavelength(s), whether or not either or both are within the visible part of the spectrum.

If outside the visible region, a detector may be employed according to the invention for detecting the radiated light. A system for determining whether or not a punctum plug is positioned within the punctal canal of a person's eye is also enclosed, including at least one optical element permitting the eye to view itself, to be viewed by the other eye, or by a second person.

DETAILED DESCRIPTION OF THE INVENTION

Broadly, this invention resides in punctum plug configurations which are more easily visualized, preferably allowing the presence and position of the plug to be seen by another person or by the recipient in a mirror. In one preferred embodiment, at least the outwardly exposed surface of the plug, or the entire plug body, is pigmented to contrast with surrounding tissue. For example, unlike existing devices, the exposed surface or plug body may be black or a saturated fluorescent color to create a more defined visual contrast.

In an alternative embodiment, the end of the plug or entire body is coated with, or otherwise contains a fluorescent dye, phosphor, phosphorescent pigment, reflective beads, quantum dots, or other material allowing the plug to be more easily visualized with appropriate illumination. In these embodiments, the plug preferably glows in the visible spectrum, though optical detectors such as a photodetector may be used if the light is outside the visible range.

Additives applicable to the invention include, but are not limited to, fluorescent and phosphorescent materials, including organic, inorganic and rare-earth phosphors, internally reflecting (i.e., TIR) beads, quantum dots, dyes and pigments. The source of illumination may be violet or ultraviolet light, or other wavelengths chosen to cause a suitable or desired excited radiation or reflection. A fluorescent lamp, light-emitting diode, hot filament or other source may be used, along with filters, beam splitters, or other optical components, as appropriate, Although use of the invention preferably permits visualization with the unaided eye, the use of instruments such as magnifiers, ophthalmoscopes and counterparts thereof, are not precluded. For example, such a device may consist of an illumination source, a beam splitting mirror, and a magnifying lens arranged such that the light from the source is separated from the light returned from the beads or dots to the eye. The device may be constructed such that one eye inspects the other or, through appropriate optics, the same eye. For example, the combination of visible light lamp and a magnifying viewer may be used to permit the eye to view itself, be viewed by the other eye, or viewed by a second person. If different illumination and response/reflective wavelengths are used, appropriate filtering may be employed to block or separate the reflected or re-radiated wavelength(s) from the illumination wavelength(s).

Figure 1:
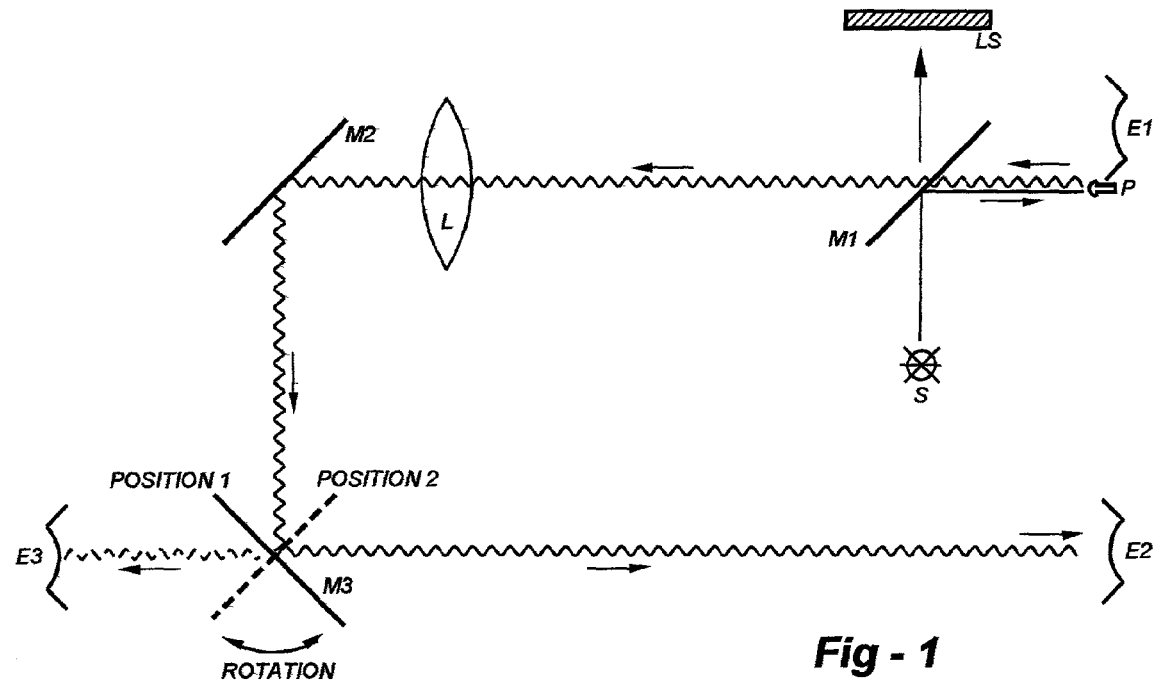
FIG. 1 is a schematic diagram of an optical aid and accompanying method according to the invention for viewing a punctum plug without interference from illumination from a primary source.
Figure 2:
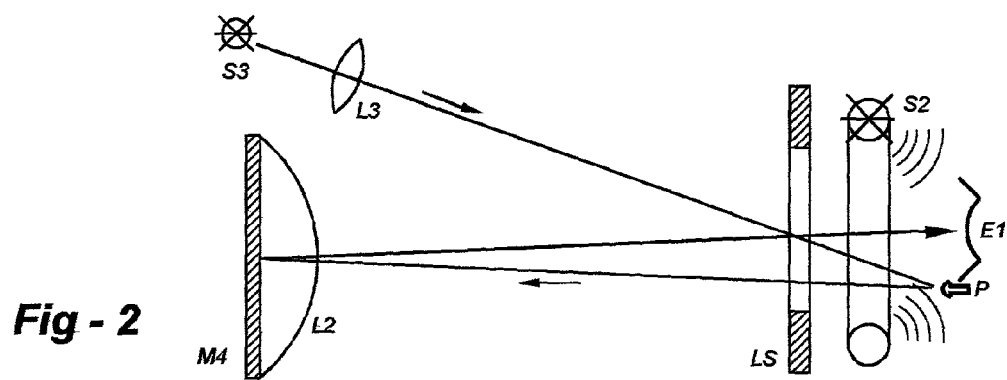
FIG. 2 is a schematic diagram of an optical aid and accompanying method according to the invention for viewing a punctum plug using the same eye into which the plug has been installed.

FIGS. 1 and 2 are schematic diagrams which illustrate optical aids and accompanying methods according to the invention for viewing punctum plugs according to the invention regardless of whether the plug retransmits light of a different wavelength or passively reflects light of the same wavelength. In the drawings, the following legend is used:

For FIG. 1:
M1=mirror-filter, reflect →, pass ~>
→=illumination, primary
~>=fluorescence light
P=punctum plug, possessing excitable agent, or non-excitable
L=magnifying lens
E1=recipient's eye under inspection
E2=recipient's other eye
E3=caregiver's eye
M2=redirection mirror
M3=rotating redirection mirror
LS=light stop
S=plug illumination source For FIG. 2:
S2=plug illuminating source, broad flood, preferably close to eye
S3=plug illumination source spot
L3=spot forming lens
L2=eye imaging lens, preferably plano-convex
M4=mirror, close to L2, or deposit on rear of L2

In FIG. 1, light from source S is reflected off element M1 illuminating plug P. Light radiated by the plug P passes through element M1 and is magnified by lens L. If a caregiver is the only individual responsible for viewing the plug, light magnified by L may be viewed directly, without the need for M2 or M3. However, in building an instrument which will allow either the same individual to view the plug with eye E2 or a caregiver to view the eye E3, mirrors M2 and M3 may be provided, with M3 having first and second positions to switch between E2 and E3. Note that element M1 may be any device operative to at least partially reflect illumination from the source and at least partially pass light reflected or emitted by the plug, and may therefore be a semi-silvered mirror, filter, simple beamsplitter, or any combination thereof.

FIG. 2 is a drawing which illustrates a configuration enabling the same eye to view a plug inserted into that eye. In this case, light from a source S2, preferably a circular source, illuminates the plug P with a light stop LS preferably being used to block direct light from S2 from reaching an observer. Alternatively, a light from source S3 may be used, preferably along with spot forming lens L3. In any case, the light radiated or reflected by the plug is redirected to the same eye, E1, using reflector M4, preferably with an imaging lens L2 to magnify the image.

I claim:

1. A punctum plug which is more easily visualized when positioned within a punctual canal, the plug comprising:
   a body having an outwardly exposed surface when so positioned; and
   a substance causing at least the outwardly exposed surface to contrast with surrounding tissue, such that the use of the substance causes the plug to be more easily visualized than if the substance were not present.

2. The punctum plug of claim 1, wherein the substance is disposed on the outwardly exposed surface.

3. The punctum plug of claim 1, wherein the substance is disposed within the plug body.

4. The punctum plug of claim 1, wherein the substance includes an organic or inorganic phosphor, a fluorescent material, reflective beads, quantum dots, a dye or pigment that contrasts with surrounding tissue.

5. The punctum plus of claim 1, wherein the plug is illuminated with light at an illumination wavelength, and wherein the substance generates radiated light at a wavelength other than the illumination wavelength.

6. The punctum plug of claim 5, wherein the illumination wavelength is in the violet or ultraviolet portion of the spectrum.

7. The punctum plug of claim 5, wherein the radiated light is in the visible spectrum.

8. The punctum plug of claim 5, wherein the radiated light is outside the visible spectrum, and further including a detector for detecting the radiated light.

* * * * *